United States Patent [19]

Semeraro et al.

[11] Patent Number: 5,051,432
[45] Date of Patent: Sep. 24, 1991

[54] HETEROCYCLIC 1,4 DIHYDROPYRIDINE DERIVATIVES

[75] Inventors: Claudio Semeraro, Bresso; Dino Micheli, Carpi; Daniele Pieraccioli; Giovanni Gaviraghi, both of Verona, all of Italy; Alan D. Borthwick, London, England

[73] Assignee: Glaxo, S.p.A., Verona, Italy

[21] Appl. No.: 587,159

[22] Filed: Sep. 19, 1990

Related U.S. Application Data

[63] Continuation of Ser. No. 287,609, Dec. 16, 1988, abandoned, which is a continuation of Ser. No. 16,589, Feb. 19, 1987, abandoned.

[30] Foreign Application Priority Data

Feb. 20, 1986 [IT] Italy ................. 19485 A/86

[51] Int. Cl.$^5$ ................. C07D 211/86; A61K 31/455
[52] U.S. Cl. ................. 514/356; 514/318; 514/343; 546/194; 546/281; 546/321
[58] Field of Search .............. 546/321, 194, 281; 514/356, 318, 343

[56] References Cited

U.S. PATENT DOCUMENTS

| | | | |
|---|---|---|---|
| 3,455,945 | 7/1969 | Loev | 546/321 |
| 4,220,649 | 9/1980 | Kojima et al. | 546/281 |
| 4,448,964 | 5/1984 | Muto et al. | 546/194 |
| 4,492,703 | 1/1985 | Goldmann et al. | 546/321 |
| 4,551,467 | 11/1985 | Wehinger et al. | 546/321 |

OTHER PUBLICATIONS

T. Kameyama et al., "Effect on Centrally Acting Muscle Relaxants on the Morphine-Induced Straub Tail Reaction in Mice," *Chemical & Pharmaceutical Bulletin*, 27 No. 5; 1426–1440 (1979).

Primary Examiner—Jane T. Fan
Attorney, Agent, or Firm—Morgan & Finnegan

[57] ABSTRACT

Compounds are described of the formula

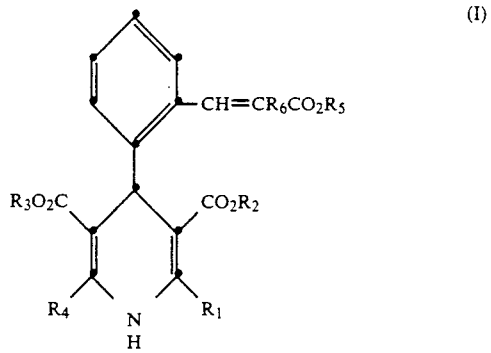

wherein
$R_1$ and $R_4$ independently represent a $C_{1-4}$ alkyl group:
$R_2$ represents a group

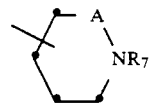

(where A is a bond or a methylene group and $R_7$ is phenyl $C_{1-4}$ alkyl; or $R_2$ represents a group $CH_2CH_2NR_8R_9$ (where $R_8$ is hydrogen or $C_{1-4}$ alkyl and $R_9$ is $C_{1-4}$ alkyl, phenyl $C_{1-4}$ alkyl or benzoyl $C_{1-4}$ alkyl); or $R_2$ represents a $C_{1-4}$ alkyl group substituted by nitrile.
$R_3$ represents a $C_{1-6}$ straight or brached alkyl chain or alkoxy group;
$R_5$ represents a straight or branched chain $C_{1-13}$ alkyl group or a $C_{5-8}$ cycloalkyl group which may be substituted by a $C_{1-3}$ alkyl substituent;
$R_6$ represents a halogen atom or a straight or. branched $C_{1-3}$ alkyl group.

The compounds represented by formula (I) reduce intracellular calcium ion concentration by limiting transmembranal calcium ion influx and thus may be useful for the treatment of cardiovascular disorders such as hypertension.

21 Claims, No Drawings

HETEROCYCLIC 1,4 DIHYDROPYRIDINE DERIVATIVES

This is a continuation of co-pending application Ser. No. 07/287,609, filed on 12/16/88 now abandoned; which is a continuation of co-pending application Ser. No. 07/016,589, filed on Feb. 19, 1987 now abandoned.

This invention relates to novel heterocyclic derivatives which have an effect on the transmembranal influx of calcium ions into the cells of cardiac and smooth muscle, to processes for the preparation thereof, to pharmaceutical compositions containing them and to their use in therapeutics.

The role of intracellular calcium ions in the control of the contractile system of cardiac and smooth muscle is well known. It has been established that compounds which limit the intracellular calcium ion concentration by preventing or reducing the transmembranal calcium ion influx in cells of the contractile system of cardiac and smooth muscle are useful in the treatment of cardiovascular disorders.

We have now found a new group of compounds which reduce intracellular calcium ion concentration by limiting transmembranal calcium ion influx and thus may be useful for the treatment of cardiovascular disorders such as hypertension, angina pectoris, myocardial ischaemia, congestive heart failure, cerebral vascular and peripheral disorders, and for the treatment of diseases characterised by reversible airway obstruction such as asthma and chronic bronchitis.

The invention thus provides for compounds of the general formula (I)

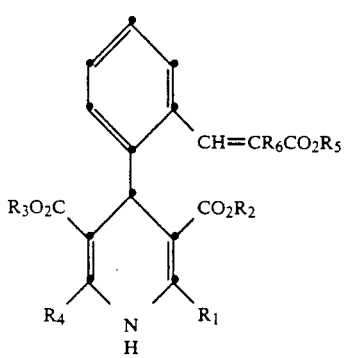

and physiologically acceptable salts thereof, in which
$R_1$ and $R_4$ independently represent a $C_{1-4}$ alkyl group;
$R_2$ represents a group

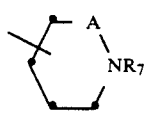

(where A is a bond or a methylene group and $R_7$ is phenyl $C_{1-4}$ alkyl); or $R_2$ represents a group $CH_2CH_2NR_8R_9$ (where $R_8$ is hydrogen or $C_{1-4}$ alkyl and $R_9$ is $C_{1-4}$ alkyl, phenyl$C_{1-4}$alkyl or benzoyl$C_{1-4}$alkyl); or $R_2$ represents a $C_{1-4}$ alkyl group substituted by nitrile;
$R_3$ represents a $C_{1-6}$ straight or branched chain alkyl or alkoxyalkyl group;

$R_5$ represents a $C_{1-13}$ straight or branched chain alkyl group or a $C_{5-8}$ cycloalkyl group which may be substituted by a $C_{1-3}$ alkyl group; and
$R_6$ represents a hydrogen or halogen atom or a $C_{1-3}$ alkyl group.

The compounds represented by formula (I) can exist in more than one isomeric and/or enantiomeric form and the invention includes all such isomers, enantiomers and mixtures thereof.

The term 'alkyl' as a group or part of a group means that the group is straight or branched.

The compounds of formula (I) in which the group $R_2$ is basic forms salts with inorganic or organic acids. Particularly suitable salts are those of physiologically acceptable inorganic and organic acids and include hydrochlorides, hydrobromides, sulphates, p-toluenesulphonates, methanesulphonates, formates, acetates, maleates, fumarates, succinates, phosphates, citrates, tartrates and benzoates.

Examples of suitable groups for $R_1$ and $R_4$ independently include methyl and ethyl groups.

Examples of suitable groups for $R_2$ include N-benzylpyrrolidino, N-benzylpiperidino, $CH_2CH_2CN$ and $CH_2CH_2NR_8R_9$ (where $R_8$ is hydrogen or methyl and $R_9$ is methyl, benzyl or benzoylethyl).

Examples of suitable groups for $R_3$ include $C_{1-4}$ straight or branched chain alkyl groups such as methyl, ethyl, isopropyl, isobutyl, t-butyl or $C_{1-4}$ alkyl (such as ethyl) substituted by a $C_{1-3}$ alkoxy (e.g. methoxy or propoxy) group.

When the group $R_5$ represents a $C_{1-13}$ alkyl group this may for example be a methyl, ethyl, propyl, isopropyl, butyl, sec butyl, isobutyl, tert butyl, pentyl, isopentyl, neopentyl, hexyl, 2,6-dimethyl-4-heptyl, octyl or a tridecyl group. When $R_5$ represents a cycloalkyl group, conveniently this represents a cyclopentyl, cyclohexyl or cycloheptyl group, which may be substituted by a methyl group.

When the group $R_6$ represents a $C_{1-3}$ alkyl group this may for example be a methyl, ethyl or n-propyl, and is preferably a methyl or ethyl group.

When the group $R_6$ represents a halogen atom this may be for example a chlorine, bromine or iodine atom, and is preferably a bromine atom.

The group $—CH=CR_6CO_2R_5$ in the compounds of formula (I) can exist in the (Z) or the (E) configuration and preferred compounds are those in which the hydrogen atom and the group $R_6$ are trans with respect to each other.

Preferably $R_1$ and $R_4$ represent methyl groups.
$R_2$ preferably represents N-benzylpiperidino, $CH_2CH_2CN$ or $CH_2CH_2NR_8R_9$ (where $R_8$ is hydrogen or methyl and $R_9$ is methyl or benzyl).
$R_3$ preferably represents $C_{1-4}$ alkyl e.g. methyl or ethyl.
$R_5$ preferably represents a $C_{2-9}$ straight or branched chain alkyl group, or more preferably tert butyl.
$R_6$ preferably represents a methyl or ethyl group or more perfectly a hydrogen atom.

Particularly preferred compounds according to the invention are
2,6-Dimethyl-4-[2-(3-(1,1-dimethylethoxy)-3-oxo-1-propenyl)phenyl]-1,4-dihydro-3,5-pyridinedicarboxylic acid, ethyl (1-benzyl-4-piperidinyl)ester;
2,6-Dimethyl-4-[2-(3-(1,1-dimethylethoxy)-3-oxo-1-propenyl)phenyl]-1,4-dihydro-3,5-pyridinedicarboxylic acid, ethyl, dimethylaminoethyl ester;

2,6-Dimethyl-4-[2-(3-(1,1-dimethylethoxy)-3-oxo-1-propenyl)phenyl]-1,4-dihydro-3,5-pyridinedicarboxylic acid, ethyl 2-cyano ethylester;

2,6-Dimethyl-4-[2-(3-(1,1-dimethylethoxy)-3-oxo-1-propenyl)phenyl]-1,4-dihydro-3,5-pyridinedicarboxylic acid, methyl (N-phenylmethyl-N-methylaminoethyl) ester; and more particularly the E isomers thereof, and their physiologically acceptable salts.

The ability of the compounds to limit or inhibit the effect of calcium ions on the tone of vascular smooth muscle maybe determined using a depolarised rabbit ear artery prepared according to the method of Towart. R. et al Br. J. Pharmacol. 1982, 75, 1508.

The antihypertensive activity of the compounds of the invention was demonstrated by intravenous and/or oral administration of the compound to male spontaneously hypertensive rats.

The compounds of the invention are thus of interest in the treatment of hypertension and diseases characterised by reversible airways obstruction such as asthma and chronic bronchitis. They are also potentially useful for the treatment of other cardiovascular disorders including angina pectoris, myocardial ischaemia, congestive heart failure, cerebral vascular and peripheral disorders.

The compounds of the invention may be formulated in a conventional manner for use with one or more pharmaceutical carriers or excipients.

Thus a further aspect of the invention includes pharmaceutical compositions the compounds of formula (I) formulated for oral, sub lingual, transdermal, parenteral or rectal administration or for administration by inhalation or insufflation.

A proposed daily dosage of active compound of the invention for the treatment of man is in the range of 0.03 mg to 100 mg, which may conveniently be administered in one or more doses. The precise dose employed will depend on the age and condition of the patient as well as the route of administration.

For oral use the compounds of the invention are conveniently administered to the human patient at a dose in the range 0.3 to 100 mg per day. For parenteral use the compounds of the invention are conveniently administered at a dose in the range of 0.03-30 mg per day.

For administration by inhalation use the compounds of the invention are conveniently administered to the human patient at a dose in the range of 0.1 mg to 10 mg per day.

For oral use the compound is preferably administered twice or more particularly once a day.

Methods for preparing the compounds of formula (I) are described below and for the intermediates described below $R_1$, $R_2$, $R_3$, $R_4$, $R_5$ and $R_6$ have the meanings defined above for compounds of formula (I) or are such groupings in a protected form unless otherwise stated.

Thus compounds of formula (I) may be prepared by reaction the α,β-unsaturated ketone (II) with the aminoester (III). The reaction is conveniently carried out in a solvent such as an alkanol, e.g. ethanol or isopropanol and preferably with heating e.g. 40°-150° C.

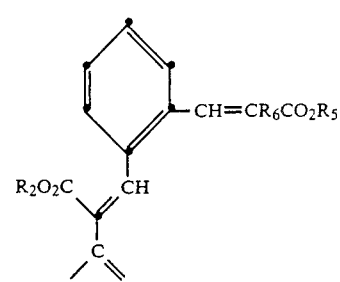

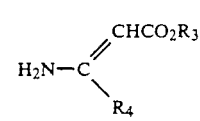

The α,β-unsaturated ketone (II) may be prepared by reacting the aldehyde (IV) with the ketoester (V), in a solvent such as an alkanol e.g. ethanol or isopropanol, preferably with heating e.g. 40°-150° C. Conveniently this reaction is carried out in the presence of a catalyst such as piperidine acetate.

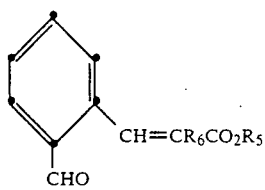
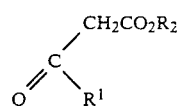

In a modification of this process for preparing compounds of formula (I), the aldehyde (IV) may be reacted with a mixture of the aminoester (III) and the ketoester (V) under the conditions previously described for the reaction of the α,β-unsaturated ketone (II) with the aminoester (III).

Compounds of formula (IV) may be prepared by reacting the bis aldehyde (VI) with the triphenylphosphorane (VII) in solvent such as methylene chloride or toluene.

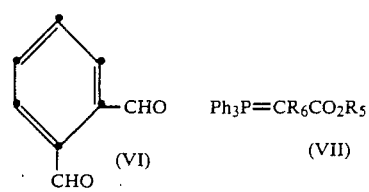

Compounds of formula (IV) may also be prepared by reacting a 2-halobenzaldehyde (VIII)

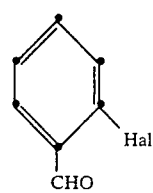

(where Hal represents a bromine or iodine atom) with an acrylic ester $CH_2=CR_6CO_2R_5$ (IX), in the presence of a catalytic amount of a palladium salt such as palladium acetate, in the presence of a suitable organic base such as a trialkylamine e.g. triethylamine or tri-n-butylamine. The reaction is also preferably carried out in the presence of a triarylphosphine such as tri-o-tolyphosphine, or more preferably, triphenylphosphine.

The reaction is conveniently carried out in a suitable solvent such as xylene or t-butyl acetate, or more conveniently in dimethylformamide or in a mixture of solvents e.g. xylene/dimethylformamide, preferably with heating. The reaction mixture is preferably heated within the temperature range of 80° C. to 150° C., more preferably at 100° C. to 110° C.

The compounds of formulae (III), (V), (VI), (VII), (VIII) and (IX) are either known compounds or may be made by analogous processes to those used for known compounds.

The following examples illustrate the invention. Temperatures are in °C.

INTERMEDIATE 1

(E)-3-(2-Formylphenyl)-2-propenoic acid, 1,1-dimethyl ethyl ester

A solution of triphenylphosphoranylidene acetic acid 1,1-dimethylethyl ester (54.7 g) in dry dichloromethane (100 ml) was added to a solution of ortho phthaldehyde (19.3 g) in dry dichloromethane at 0° C. in 15 minutes. The solvent was evaporated and the oil taken up with diethyl ether. The solid triphenylphosphine oxide was filtered, washed with ether and the filtrate evaporated to dryness to give a yellow oil (36 g) which was eluted on a silica gel column (petrol ether/diethyl ether, 7:3), to give the title compound as a colourless oil (21.4 g). T.l.c. (Petrol ether/diethyl ether, 1:1) Rf 0.45.

INTERMEDIATE 2

2-(2-(3-(1,1-Dimethylethoxy)-3-oxo-1-propenyl)-phenyl)methylene-3-oxo-butanoic acid, ethyl ester A solution of piperidine (0.07 ml) and acetic acid (0.04 ml) in isopropanol (0.58 ml) was added to a solution of Intermediate 1 (3 g) and ethyl acetoacetate (0.69 g) in isopropanol (8.5 ml). The mixture was stirred at 60° for 1 h, then the solvent was evaporated and the residue taken up with ether. The solution was washed with 1N HCl, saturated bicarbonate solution and brine and dried over $Na_2SO_4$. Evaporation of the solvent gave the title compound as an oil (4.07 g; mixture of E and Z isomers). T.l.c. (petrol ether/ethyl acetate 4:1) Rf 0.26; Rf 0.35.

EXAMPLE 1

2,6-Dimethyl-4(E)-[2-(3-(1,1-dimethylethoxy)-3-oxo-1-propenyl)phenyl]-1,4-dihydro-3,5-pyridinedicarboxylic acid, ethyl, dimethylaminoethyl ester, hydrochloride A solution of Intermediate 1 (9.29 g), 3-amino-2-butenoic acid ethyl ester (5.18 g) and 3-oxo-butanoic acid, dimethylamino ethyl ester (7 g) in ethanol (25 ml) was refluxed for 15 h. After evaporation of the solvent the residue was purified by column chromatography on silica gel eluting with methylene chloride/methanol 9:1 to give the free base of the title compound (0.6 g). A solution of free base (0.25 g) and 0.1N HCl (4.9 ml) in acetone (9 ml) was stirred for five minutes. After evaporation of the solvent the residue was crystallized from petrol to give the title compound (0.2 g) as a yellow solid. M.p. 195°–196°. T.l.c. (methylene chloride/methanol 9:1) Rf 0.28.

Similarly prepared were Examples 2 and 3:

EXAMPLE 2

2,6-Dimethyl-4(E)-[2-(3-(1,1-dimethylethoxy)-3-oxo-1-propenyl)phenyl]-1,4-dihydro-3,5-pyridinedicarboxylic acid, methyl, N-phenylmethyl-N-methylaminoethyl ester, hydrochloride (0.6 g)

From Intermediate 1 (2.32 g), 3-amino-2-butenoic acid, methyl ester (1.15 g) and 3-oxo-butanoic acid (2-N-phenylmethyl-N-methylaminoethyl) ester (2.5 g). M.p.=120°–130° dec. T.l.c. (ethyl acetate/$CH_2Cl_2$ 9:1) Rf 0.5.

EXAMPLE 3

2,6-Dimethyl-4(E)-[2-(3-(1,1-Dimethylethoxy)-3-oxo-1-propenyl)phenyl]-1,4-dihydro-3,5-pyridinedicarboxylic acid, ethyl 2-cyanoethyl ester (2.4 g)

From Intermediate 1 (10.5 g), 3-oxo-butanoic acid, ethyl ester (5.85 g) and 3-amino-2-butenoic acid (2-cyanoethyl) ester (7.5 g). M.p. 168°–169°. T.l.c. (cyclohexane/ethyl acetate 1:1) Rf 0.29.

EXAMPLE 4

2,6-Dimethyl-4(E)-[2-(3-(1,1-dimethylethoxy)-3-oxo-1-propenyl)phenyl]-1,4-dihydro-3,5-pyridinedicarboxylic acid, ethyl (1-benzyl-4-piperidinyl)ester, hydrochloride A solution of Intermediate 2 (3 g) and 3-amino-2-butenoic acid(1-benzyl-4-piperidinyl) ester (2.4 g) in ethanol (40 ml) was refluxed for 11 h. After evaporation of the solvent the residue was purified by column chromatography on silica gel eluting with ethyl acetate/petrol 6:4 to give the free base of the title compound (0.73 g). A solution of free base (0.73 g) and 0.1N HCl (12.15 ml) in acetone (10 ml) was stirred for 5 min. After evaporation of the solvent the residue was crystallised from petrol to give the title compound (0.63 g) as a yellow solid. M.p. 138°–140°. T.l.c. (ethyl acetate/petrol 9:1) Rf 0.44

We claim:

1. A compound of the formula (I):

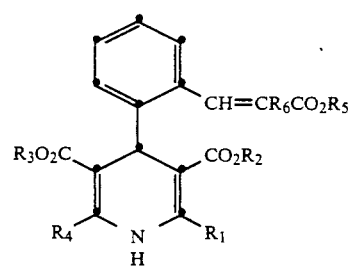

or a physiologically acceptable salt thereof, in which
$R_1$ and $R_4$ independently represent a $C_{1-4}$ alkyl group;
$R_2$ represents a group

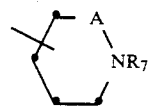

where A is a bond or a methylene group and $R_7$ is a phenyl $C_{1-4}$ alkyl group, or $R_2$ represents the group $CH_2CH_2NR_8R_9$ where $R_8$ is hydrogen or a $C_{1-4}$ alkyl group and $R_9$ is a $C_{1-4}$ alkyl group, a phenyl $C_{1-4}$ alkyl group or a benzoyl $C_{1-4}$ alkyl group, or $R_2$ represents a $C_{1-4}$ alkyl group substituted by nitrile;

$R_3$ represents a $C_{1-6}$ straight or branched chain alkyl or alkoxyalkyl group;

$R_5$ represents a $C_{1-13}$ straight or branched chain alkyl group or a $C_{5-8}$ cycloalkyl group which may be substituted by a $C_{1-3}$ alkyl group; and $R_6$ represents hydrogen or a halogen.

2. A compound as claimed in claim 1 in which $R_1$ and $R_4$ represent methyl groups.

3. A compound as claimed in claim 1 in which $R_2$ represents the group N-benzylpiperidino, $CH_2CH_2CN$ or $CH_2CH_2NR_8R_9$ where $R_8$ is hydrogen or a methyl group and $R_9$ is a methyl or benzyl group.

4. A compound as claimed in claim 1 in which $R_3$ represents a methyl or ethyl group.

5. A compound as claimed in claim 1 in which $R_5$ represents a $C_{2-9}$ straight or branched chain alkyl group.

6. A compound as claimed in claim 5 in which $R_5$ represents a tert-butyl group.

7. A compound as claimed in claim 1 in which $R_6$ represents hydrogen.

8. A compound selected from 2,6-Dimethyl-4-[2-(3-(1,1-dimethylethoxy)-3-oxo-1propenyl)phenyl]-1,4-dihydro-3,5-pyridinedicarboxylic acid, ethyl(1-benzyl-4-piperidinyl)ester;

2,6-Dimethyl-4-[2-(3-(1,1-dimethylethoxy)-3-oxo-1-propenyl)phenyl]-1,4-dihydro-3,5-pyridinedicarboxylic acid, ethyl, dimethylaminoethylester;

2,6-Dimethyl-4-[2-(3-(1,1-dimethylethoxy)-3-oxo-1propenyl)phenyl]-1,4-dihydro-3,5-pyridinedicarboxylic acid, ethyl2-cyanoethylester;

2,6-Dimethyl-4-[2-(3-(1,1-dimethylethoxy)-3-oxo-1-propenyl)phenyl]-1,4-dihydro-3,5-pyridinedicarboxylic acid, methyl-N-phenylmethyl-N-methylaminoethylester; or a physiologically acceptable salt thereof.

9. A compound as claimed in claim 1 in which the hydrogen and the group $R_6$ in the moiety $-CH=CR_6CO_2R_5$ are trans with respect to each other.

10. A compound as claimed in claim 1 in which $R_1$ and $R_4$ represent methyl groups; $R_2$ represents the group N-benzylpyrrolidino, N-benzylpiperidino, $CH_2CH_2CN$ or $CH_2CH_2NR_8R_9$ where $R_8$ is hydrogen or a methyl group and $R_9$ is a methyl, benzyl or benzoylethyl group; $R_3$ represents a methyl or ethyl group; $R_5$ represents a $C_{2-9}$ straight or branched chain alkyl group; and $R_6$ represents a hydrogen.

11. A compound as claimed in claim 10 in which $R_2$ represents the $CH_2CH_2NR_8R_9$ group where $R_8$ is hydrogen and $R_9$ is the methyl group.

12. A compound as claimed in claim 10 in which $R_5$ represents a $C_{2-9}$ branched chain alkyl group.

13. A compound as claimed in claim 10 in which $R_5$ represents a $C_{2-9}$ straight chain alkyl group.

14. A compound as claimed in claim 10 in which the hydrogen and the group $R_6$ in the moiety $-CH=CR_6CO_2R_5$ are trans with respect to each other.

15. A compound as claimed in claim 10 in which $R_2$ represents the group $CH_2CH_2NR_8R_9$ where $R_8$ is the methyl group and $R_9$ is the benzyl group.

16. A compound as claimed in claim 10 in which $R_2$ represents the group $CH_2CH_2CN$.

17. A compound as claimed in claim 10 in which $R_2$ represents the group N-benzylpiperidino.

18. A pharmaceutical composition comprising an effective amount of a compound as claimed in claim 1 in association with a pharmaceutically acceptable carrier or diluent.

19. A composition as in claim 18 in a form suitable for oral, sublingual, transdermal, parenteral or rectal administration, or for administration by inhalation or insufflation.

20. A pharmaceutical composition as claimed in claim 18 wherein the compound is used in an amount between about 0.03 mg and about 100 mg.

21. A composition for treating cardiovascular disorders resulting from transmembranal calcium ion flux comprising an effective amount of at least one compound as defined in claim 18 and a physiologically acceptable carrier.

* * * * *